United States Patent
Woloszko et al.

(10) Patent No.: US 10,828,081 B2
(45) Date of Patent: Nov. 10, 2020

(54) METHODS AND SYSTEMS RELATED TO ELECTROSURGICAL WANDS

(71) Applicant: ArthroCare Corporation, Austin, TX (US)

(72) Inventors: Jean Woloszko, Austin, TX (US); Johnson E. Goode, Austin, TX (US); David A. Cox, Austin, TX (US); Philip M. Tetzlaff, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 320 days.

(21) Appl. No.: 15/623,697

(22) Filed: Jun. 15, 2017

(65) Prior Publication Data

US 2017/0290619 A1 Oct. 12, 2017

Related U.S. Application Data

(62) Division of application No. 14/189,280, filed on Feb. 25, 2014, now Pat. No. 9,693,818.

(Continued)

(51) Int. Cl.
*A61B 18/14* (2006.01)
*A61B 18/00* (2006.01)
*A61B 18/04* (2006.01)

(52) U.S. Cl.
CPC .......... *A61B 18/042* (2013.01); *A61B 18/14* (2013.01); *A61B 18/148* (2013.01);

(Continued)

(58) Field of Classification Search
CPC .... A61B 18/14; A61B 18/042; A61N 1/0565; A61N 1/036185; A61N 1/05
See application file for complete search history.

(56) References Cited

U.S. PATENT DOCUMENTS

2004/0230262 A1 11/2004 Sartor
2005/0212870 A1 9/2005 Chiao
(Continued)

FOREIGN PATENT DOCUMENTS

GB 2451623 2/2009
GB 2477353 8/2011

OTHER PUBLICATIONS

Office Action for German Patent Application No. 102014003288.4 dated Jun. 26, 2018, 12 pages.

(Continued)

*Primary Examiner* — Linda C Dvorak
*Assistant Examiner* — Annabeth E Rodriguez
(74) *Attorney, Agent, or Firm* — Norman F. Hainer, Jr.

(57) ABSTRACT

Electrosurgical wands. At least some of the illustrative embodiments are electrosurgical wands having features that reduce contact of tissue with an active electrode of a wand, decrease the likelihood of clogging, and/or increase the visibility within surgical field. For example, wands in accordance with at least some embodiments may comprise stand-offs, either along the outer perimeter of the active electrode, or through the main aperture in the active electrode, to reduce tissue contact. Wands in accordance with at least some embodiments may implement slots on the active electrodes to increase bubble aspiration to help keep the visual field at the surgical site clear. Wands in accordance with at least some embodiments may implement aspiration flow pathways within the wand that increase in cross-sectional area to reduce the likelihood of clogging.

15 Claims, 11 Drawing Sheets

Related U.S. Application Data

(60) Provisional application No. 61/773,917, filed on Mar. 7, 2013.

(52) U.S. Cl.
CPC .......... *A61B 2018/00577* (2013.01); *A61B 2018/00583* (2013.01); *A61B 2018/00589* (2013.01); *A61B 2218/002* (2013.01); *A61B 2218/007* (2013.01)

(56) References Cited

U.S. PATENT DOCUMENTS

| | | | |
|---|---|---|---|
| 2005/0234446 A1* | 10/2005 | Van Wyk | A61B 18/1485 606/41 |
| 2008/0097476 A1 | 4/2008 | Peh | |
| 2008/0167645 A1* | 7/2008 | Woloszko | A61B 18/1206 606/40 |
| 2009/0048592 A1* | 2/2009 | Thomas | A61B 18/148 606/33 |
| 2010/0160910 A1* | 6/2010 | Kramer | A61B 18/1482 606/41 |
| 2012/0191089 A1 | 7/2012 | Gonzalez | |

OTHER PUBLICATIONS

Office Action for U.S. Appl. No. 15/715,383 dated Jun. 28, 2019, 9 pages.

\* cited by examiner

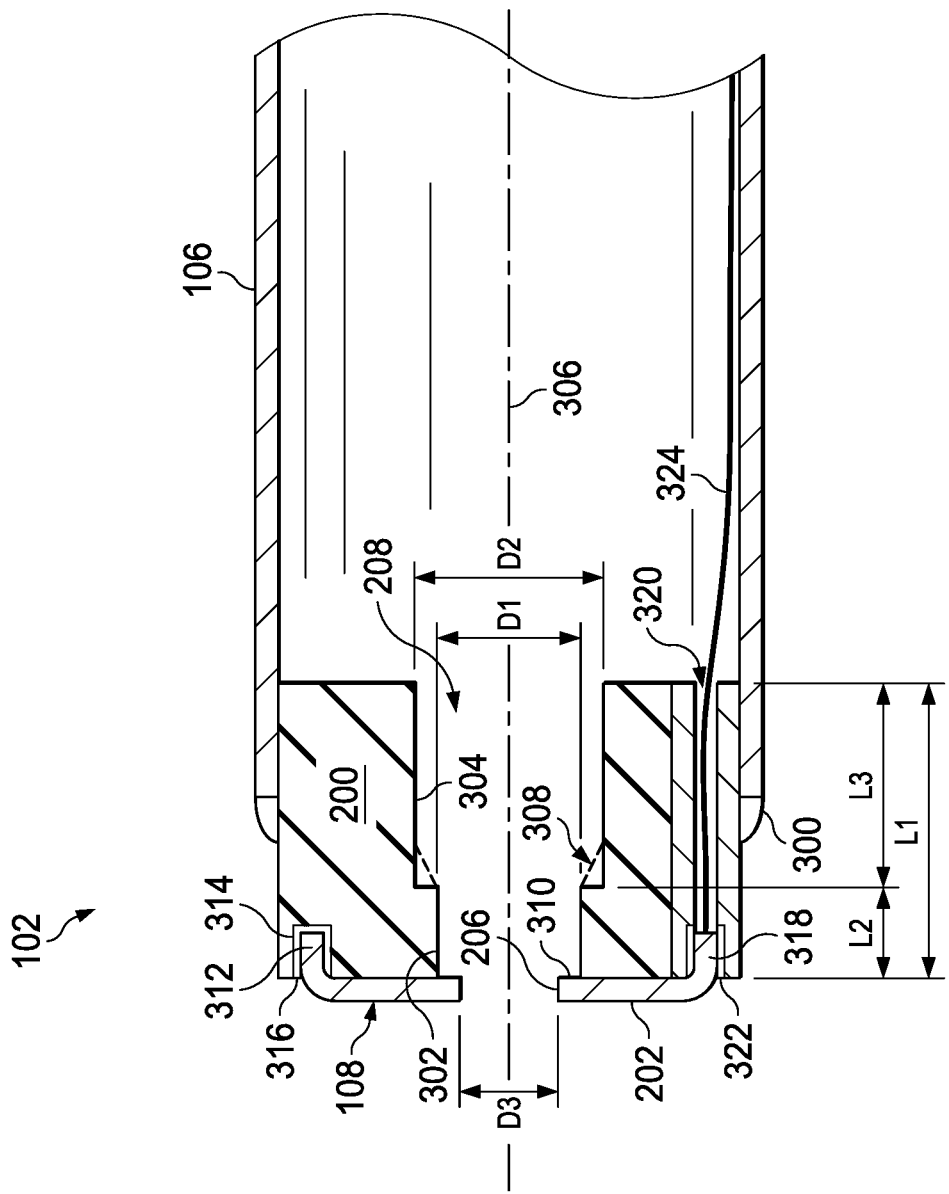

METHODS AND SYSTEMS RELATED TO ELECTROSURGICAL WANDS

CROSS-REFERENCE TO RELATED APPLICATIONS

This application is a divisional application of U.S. application Ser. No. 14/189,280 filed Feb. 25, 2014, which claims priority to U.S. provisional application No. 61/773,917, filed Mar. 7, 2013, entitled "Method and Systems Related to Electrosurgical Wands."

BACKGROUND

Electrosurgical systems are used by physicians to perform specific functions during surgical procedures. For example, in an ablation mode electrosurgical systems use high frequency electrical energy to remove soft tissue such as sinus tissue, adipose tissue or other tissue such as meniscus, or cartilage or synovial tissue in a joint.

BRIEF DESCRIPTION OF THE DRAWINGS

For a detailed description of exemplary embodiments, reference will now be made to the accompanying drawings in which:

FIGS. 3a and 3b shows a cross-sectional elevation view a distal end of a wand in accordance with at least some embodiments;

NOTATION AND NOMENCLATURE

Figure 1:
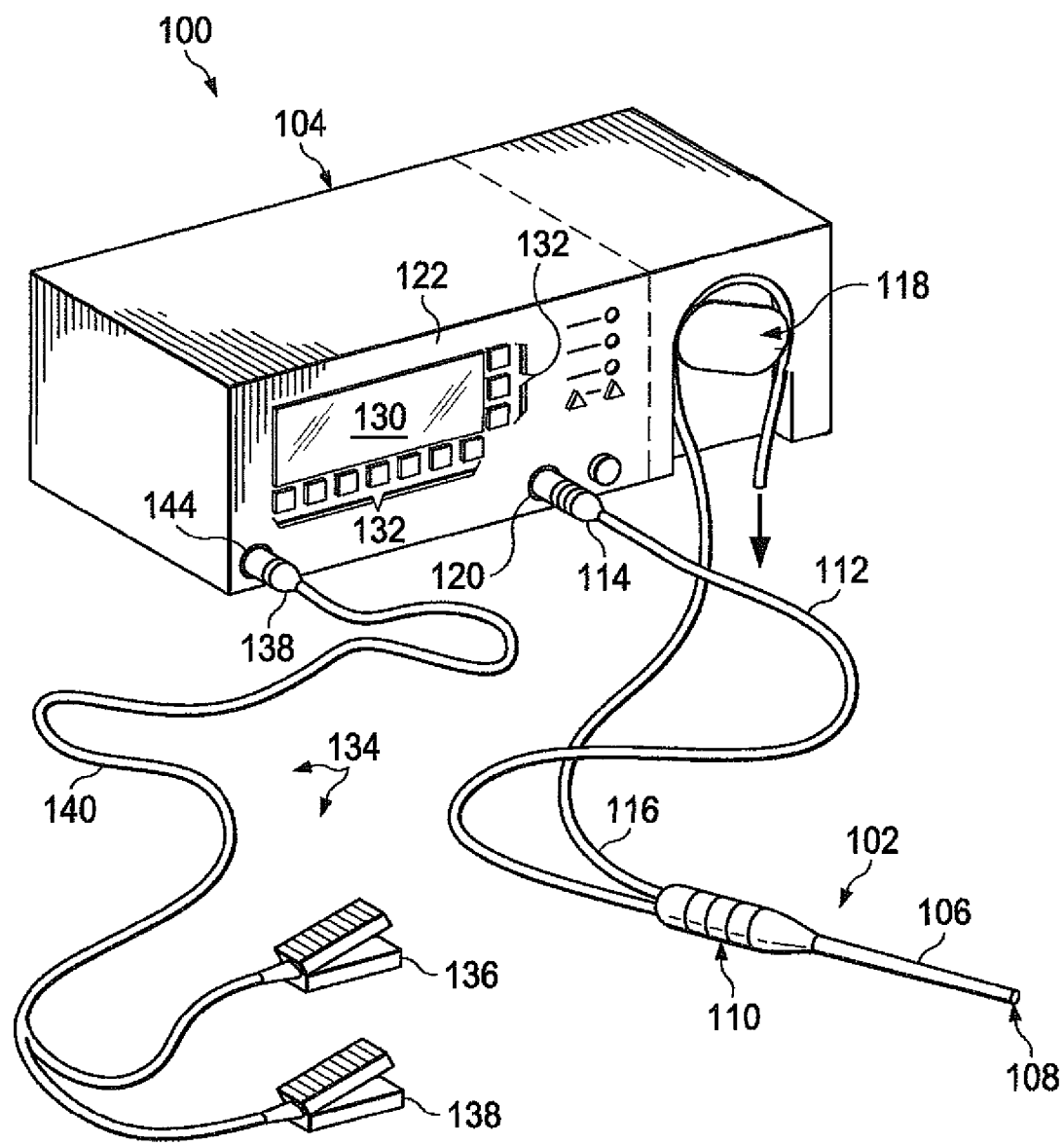
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment, and/or an electrode having a voltage induced thereon by a voltage generator.

"Active terminal" shall mean an electrical connection to a transformer that is configured to couple to an active electrode of an electrosurgical wand.

"Return electrode" shall mean an electrode of an electrosurgical wand which serves to provide a current flow path for electrons with respect to an active electrode, and/or an electrode of an electrosurgical wand which does not itself produce an electrically-induced tissue-altering effect on tissue targeted for treatment.

"Return terminal" shall mean an electrical connection to a transformer that is configured to couple to a return electrode of an electrosurgical wand.

"Plasma" shall mean a low temperature highly ionized gas formed within vapor bubbles or a vapor layer that is capable of emitting an ionized discharge.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate housing or elongate shaft 106 that defines distal end 108. The elongate shaft 106 further defines a handle or proximal end 110, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to provide aspiration at the distal end 108 of the wand. In accordance with various embodiments, the tubular member 116 couples to a peristaltic pump 118, which peristaltic pump 118 is illustratively shown as an integral component with the controller 104. In other embodiments, an enclosure for the peristaltic pump 118 may be separate from the enclosure 122 for the controller 104 (as shown by dashed lines in the figure), but in any event the peristaltic pump is operatively coupled to the controller 104. In the context of the various embodiments, the peristaltic pump 118 creates a volume-controlled aspiration from a surgical field at the distal end 108 of the wand 102.

Still referring to FIG. 1, a display device or interface device 130 is visible through the enclosure 122 of the controller 104, and in some embodiments a user may select operational modes of the controller 104 by way of the interface device 130 and related buttons 132. In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the operational mode. For example, pedal device 136 may be used for on-off control of the application of radio frequency (RF) energy to the wand 102. Further, pedal device 138 may be used to control and/or set the mode of ablation of the electrosurgical system. In certain embodiments, control of the various operational or performance aspects of controller 104 may be activated by selectively depressing finger buttons located on handle 110 of wand 102 (the finger buttons not specifically shown so as not to unduly complicate the figure).

The electrosurgical system 100 of the various embodiments may have a variety of operational modes. One such mode employs Coblation® technology. In particular, the assignee of the present disclosure is the owner of Coblation® technology. Coblation® technology involves the application of RF energy between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracelluar or intracellular fluid. In other embodiments, the electrically conductive fluid may be a liquid or gas, such as isotonic saline. In some embodiments the electrically conductive fluid is delivered in the vicinity of the active electrodes and/or to the target site by the wand 102.

When the electrically conductive fluid is heated to the point that the atoms of the fluid vaporize faster than the atoms condense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation® mode, the electrosurgical system 100 of FIG. 1 is also useful for sealing larger arterial vessels (e.g., on the order of about 1 millimeter (mm) in diameter), when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may also have a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons.

Figure 2A:
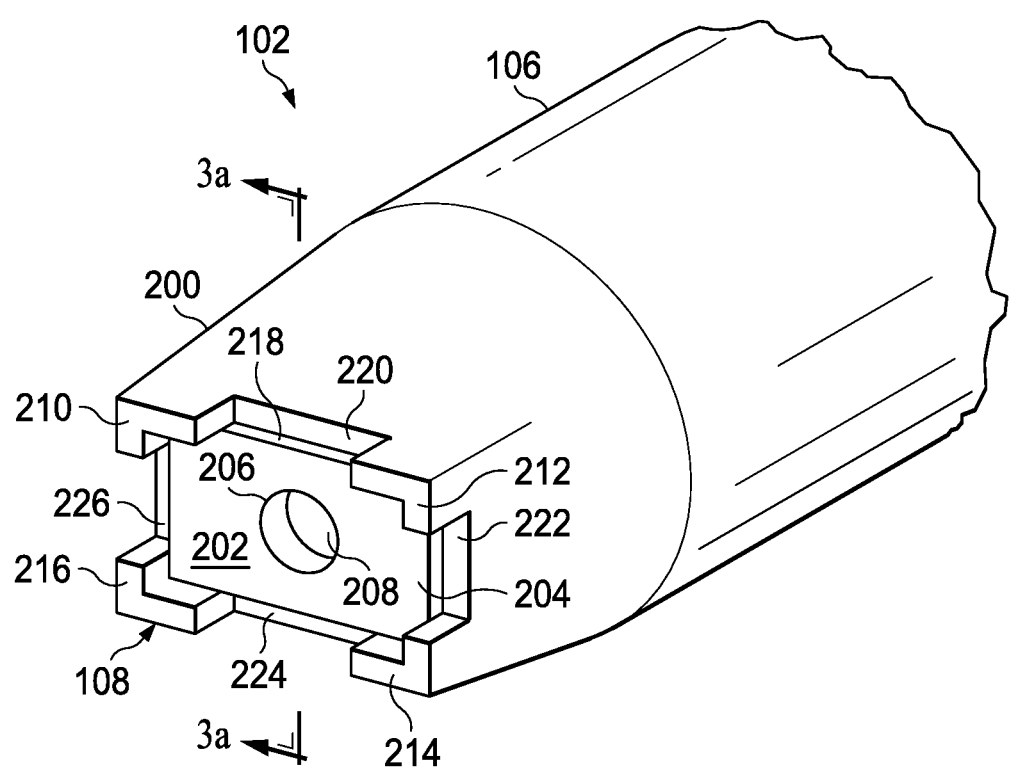
FIGS. 2a, 2b, and 2c show a perspective view the distal end of a wand in accordance with at least some embodiments.
Figure 2B:
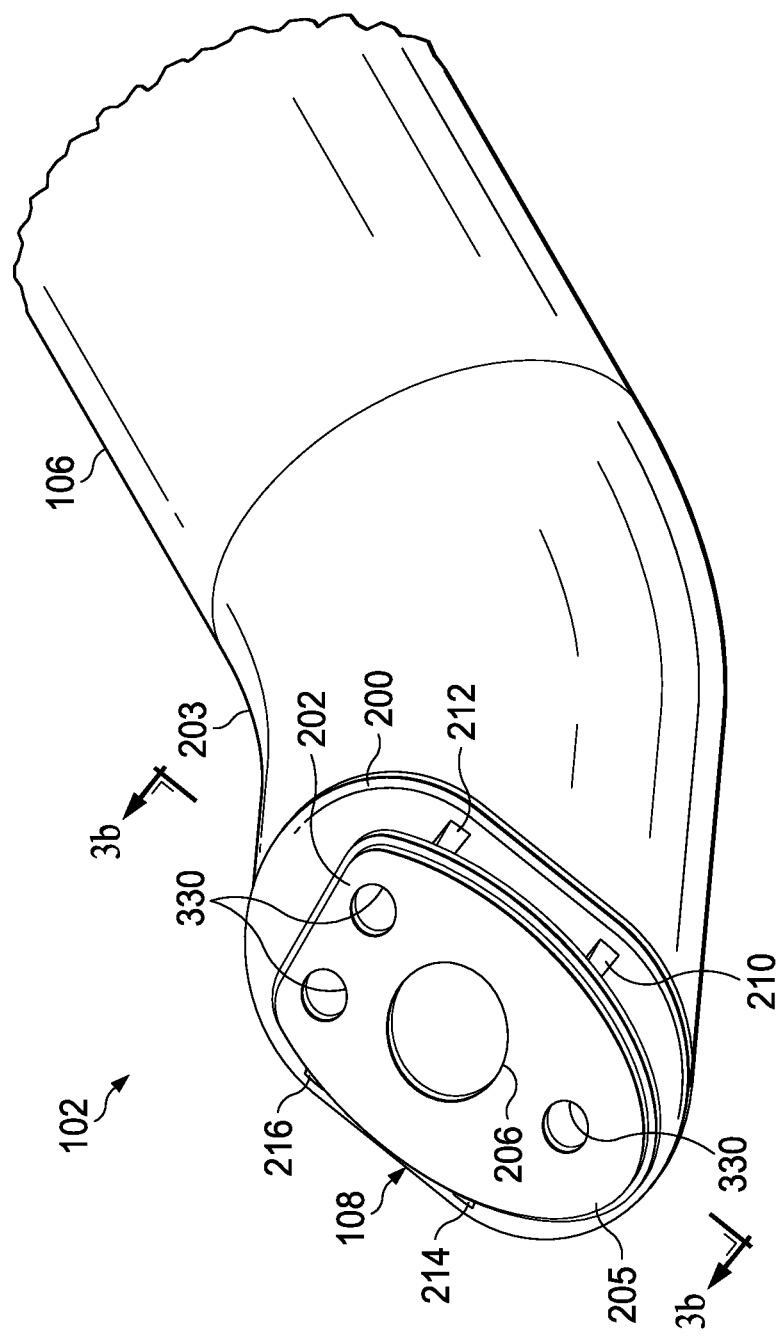
Figure 2C:
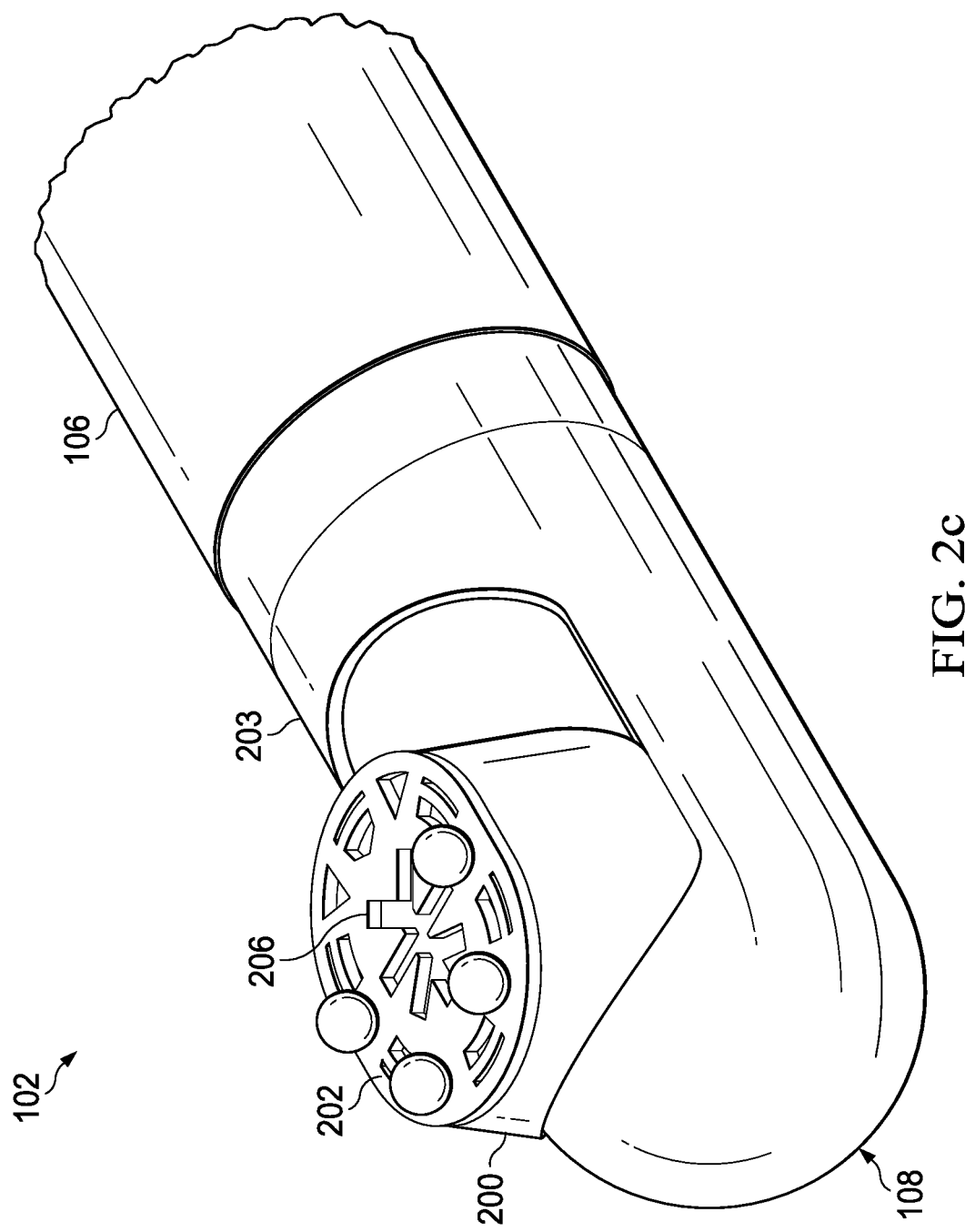

FIGS. 2a, 2b, and 2c illustrate a perspective view of the distal end 108 of wand 102 in accordance with example systems. In the illustrated embodiment the elongate shaft 106 is made of a metallic material (e.g., Grade TP304 stainless steel hypodermic tubing), and in some cases the elongate shaft 106 also defines a return electrode for the system. As illustrated, the elongate shaft 106 may define a circular cross-section at least at the distal end 108. The wand 102 shown in FIG. 2c having a circular cross-section with the active electrode 202 oriented 90° from the shaft 106 axis may be particularly suited for surgical procedures involving the shoulder, where the space within which the wand is inserted is not as limited. However, in other embodiments, such as wands designed for surgical procedures involving the knee, the cross-sectional shape of the elongate shaft 106 may be that of an oval with the active electrode 202 oriented 50° from the shaft 106 axis to provide for a lower wand distal end profile in order to accommodate space restrictions and posterior anatomy access, as shown in FIG. 2b. For embodiments where the cross-sectional shape of the elongate shaft 106 is circular, the outside diameter may be on the order of about 3 millimeters (mm), but larger and smaller dimensions may be used. For embodiments where the cross-sectional shape of the elongate shaft 106 is more oval, a larger comparable surface area of active electrode 202 is provided, whereby the largest outside diameter may be on the order of about 3 mm, and the smaller outside diameter on the order of about 2 mm, but again larger and smaller dimensions may be used.

In embodiments where the elongate shaft is metallic, the distal end 108 may further comprise a non-conductive spacer 200 coupled to the elongate shaft 106. In some cases the spacer 200 is ceramic, but other non-conductive materials resistant to degradation when exposed to plasma may be equivalently used (e.g., glass). The spacer 200 may couple to the elongate shaft 106 in any suitable manner, such as telescoping within an inside diameter of the elongate shaft 106 (as shown), by telescoping over the elongate shaft 106, and/or by use of adhesive. The spacer 200 supports at least one active electrode 202 constructed of metallic material. The spacer 200 thus electrically insulates the active electrode 202 from the elongate shaft 106, which elongate shaft 106 may act as the return electrode. In other embodiments, only a portion of elongate shaft 106 is exposed to act as return electrode 203.

The illustrative active electrode defines an exposed outer surface 204, as well as an inner surface (not visible in FIGS. 2a-c) that abuts the spacer 200. In some embodiments, such as that shown in FIG. 2b, active electrode defines an exposed edge surface 205 to allow a side ablative effect on certain more sensitive tissue types such as cartilage. The active electrode 202 further comprises at least one aperture 206 that is fluidly coupled to the flexible tubular member 116 (not shown in FIGS. 2a-c). Likewise, the spacer 200 has an aperture 208 that is also fluidly coupled to the flexible tubular member 116. As illustrated, the apertures 206 and 208 are at least partially aligned such that fluid and/or tissue may be drawn through the apertures into a fluid conduit within the elongate shaft. Various relationships of the apertures 206 and 208 are discussed more below.

Implementing a system with volume controlled aspiration through the apertures enables significantly larger aperture size than the related-art. That is, given the poor vacuum control provided by vacuum sources available in the related-art, wands of the related-art attempt to impose upper limits on flow of fluids by limiting the size of the aspiration aperture. In the related art, for example, a circular aperture diameter of 0.75 mm is considered the upper limit of aperture diameter. However, given that the various embodiments control the volume flow rate by other mechanisms, such control of the volume flow rate enables significantly larger aperture sizes. For example, in illustrative embodiments comprising a circular aperture 206 the diameter may be between including 0.79 mm to 1.4 mm, and in a particular embodiment 1.2 mm. Moreover, and as discussed more below, the diameter of the illustratively circular aperture through the spacer 200 may be larger than the diameter of aperture 206. Aperture 206 may comprise various additional shapes, such as star shape or asterisk shaped (see FIG. 2c) in certain embodiments.

Still referring to FIGS. 2a-c, in some example electrosurgical procedures it may be beneficial to limit the ability of the active electrode 202 to physically contact the target tissue. In such situations, the distal end 108 of the wand 102 may implement one or more standoffs. In the particular embodiment shown in FIGS. 2a and 2b, four such standoffs 210, 212, 214, and 216 are illustrated. Each standoff is constructed of a non-conductive material, such as the same material as the spacer 200. In some cases, the standoffs 210, 212, 214, and 216 are integrally constructed with the spacer 200 (i.e., the spacer and standoffs are a single element), but in other cases the standoffs are separately created and coupled to the spacer 200. The active electrode 202 defines an outer perimeter 218, and the illustrative standoffs are disposed proximate to the outer perimeter 218 (e.g., within 0.1 mm of the outer perimeter 218). In some cases, the standoffs abut the outer perimeter.

In accordance with at least some embodiments, the standoffs 210, 212, 214, and 216 provide a predetermined spacing above the outer surface 204 of the active electrode 202. Consider, for example, that the outer surface 204 of the active electrode 202 defines a plane. In at least some embodiments, the standoffs 210, 212, 214, and 216 protrude through the plane defined by the active electrode by at least 0.1 mm. Longer or shorter protrusions through the plane defined by the outer surface 204 of the active electrode 202 are also contemplated.

Moreover, while in some cases the standoffs may fully encircle the outer perimeter 218 of the active electrode 202, in other cases the standoffs have gaps or "cut outs". In particular, in the illustrative case of FIG. 2a, four such gaps 220, 222, 224, and 226 are shown. The inventors of the present specification have found that such gaps aid in various aspects of the surgical procedures without significantly affecting the ability of the standoffs 210, 212, 214, and 216 to reduce the likelihood of the active electrode directly contacting tissue at the target site. The length of each "cut out", or alternatively stated an amount the standoffs 210, 212, 214, and 216 encompass the electrode, may be different for each wand. In some cases, however, the standoffs encompass at least 25% of the outer perimeter 218 of the active electrode 202, and as shown about 40% of the outer perimeter 218 of the active electrode 202. Furthermore, in some instances standoffs 210, 212, 214, and 216 may be effective in protecting the active electrode 202 from "washout" of the plasma formed on some portion of active electrode 202 from the suction flow directing toward aperture 206 by deflecting flow over some areas of the active electrode 202 screen.

FIG. 3a shows a side elevation, cross-sectional view (taken along line 3-3 of FIG. 2a) of the distal end 108 of the wand 102 in accordance with at least some embodiments. In particular, FIG. 3a shows the active electrode 202 abutting the spacer 200. Spacer 200 is shown telescoped within the internal diameter of the elongate housing 106, and in some cases the spacer may be at least partially held in place by an adhesive 300. FIG. 3a also shows the aperture 206 through the active electrode 202, as well as the aperture 208 through the spacer 200. However, as illustrated in FIG. 3a, the aperture 208 in accordance example systems defines a distal section 302 and a proximal section 304. The distal section 302 defines a cross-sectional area (e.g., a cross-sectional area measured normal to the central axis 306) which is smaller than the cross-sectional area of the proximal section 304 (e.g., also measured normal to the central axis 306). In the illustrative case of the distal section 302 and proximal section 304 defining circular apertures, the distal section 302 defines a circular through bore having a diameter D1, and the proximal section 304 defines a circular counter-bore having a diameter D2, where D2 is larger than D1. Moreover, overall the spacer 200 defines an axial length L1, while the proximal section 304 defines an axial length L3 and the distal section 302 defines an axial length L2. The transition 308 between the distal section 302 and the proximal section 304 (i.e., the shoulder region) is shown to have a rectangular cross section, but less abrupt transitions 308 are also contemplated, such as a transition defining a conic frustum (illustrated by dashed lines).

In accordance with at least some embodiments, the combination of the distal section 302 and proximal section 304 create a constriction in proximity to the active electrode 202 (and thus the plasma). The constriction created by the interplay between the distal section 302 and the proximal section 304 illustrates an operational philosophy implemented in example systems. In particular, in the related-art the operational philosophy was that, to avoid clogging of the aspiration aperture and/or lumen (i.e., the aspiration path), the goal of the tissue ablation was to create tissue pieces significantly smaller than the smallest internal diameter encountered in the aspiration path. For this reason, many related-art devices utilize a metallic "screen" over the aperture such that plasma is created in such a way as to create the small tissue pieces. Unlike the related-art operational philosophy, however, example systems described in this specification operate under the philosophy that the tissue only needs to be broken into pieces just small enough to pass through the constriction presented by the distal section 302 of the aperture 208. The aperture 208 opens or widens behind the distal section 302, and thus if tissue can fit though the distal section 302, the tissue is likely then to traverse the entire aspiration path without clogging.

The operational philosophy is aided by the cross-sectional area of the aperture 206 through the example active electrode. In particular, and as illustrated, the cross-sectional area of the aperture 206 is smaller than the distal section 302 of the aperture 208. Again in the illustrative case of the aperture 206 being circular or star shaped, the diameter D3 of the aperture 206 is smaller than the diameter D1 of the distal section 302 of the aperture 208. Thus, a piece of tissue need only be small enough in any two dimensions to fit through the aperture 206 (e.g., for an elongated piece of tissue, the smallest two dimensions), and thereafter will encounter only greater cross-sectional area as the tissue moves through the aspiration path. It is noted, however, that the active electrode 202 is subject to etching during use, and thus the longer the wand 102 is used in a plasma mode, the larger the cross-sectional area of the aperture 206 becomes. In most cases, the expected use time of a wand is known in advance, and the cross-sectional area of the aperture 206 is selected such that, at the end of the expected use time, the cross-sectional area of the aperture 206 will be smaller or equal to the cross-sectional area of the distal section 302 of the aperture 208.

In accordance with example systems, the difference in cross-sectional area as between the distal section 302 and proximal section 304 may be between and including one percent (1%) and thirty percent (30%), and in a particular case at least twenty percent (20%). In illustrative embodiments where the both aperture 206 through the active electrode 202 and the aperture 208 are circular, the initial diameter of the aperture 206 may be about 1.2 mm, the diameter of the distal section 302 may be about 1.4 mm, and the diameter of the proximal section 304 may be about 1.65 mm. The overall length of the spacer 200 may be different for wands intended for different surgical procedures (e.g., knee as opposed to shoulder), but in some cases the overall axial length L1 of the spacer may be in the range of 2.0 mm to 3.0 mm, and the axial length L2 of the distal section 302 may be in the range of 1.0 mm to 1.5 mm. Other sizes may be equivalently used. Additionally, the internal configuration of spacer 200 may be varied for different wand configurations (e.g., shoulder wands with electrode 202 oriented 90° from shaft 106 axis) where aperture 206 is transverse to central axis 306, such that distal section 302 is aligned with aperture 206 and proximal section 304 is aligned with central axis 306. In these configurations in particular, the use of conic transition 308 where making the right angle turn from distal section 302 to proximal section 304 is advantageous.

Considering that the controller 104, and more particularly the peristaltic pump 118, may control the volume flow rate through the wand, the various dimensions of the apertures may be alternatively thought of as providing different velocities of the fluid through each portion. That is, for an overall constant volume flow rate of fluid induced by the peristaltic pump 118, hydrodynamic principles teach that velocity of fluid (and tissue) through each aperture will be different to achieve the same volume flow rate. Thus, because of the relationships of the cross-sectional areas of the aperture 206 and sections of the aperture 208, the velocity of fluid flow through each aperture will be different for a constant volume flow rate at the peristaltic pump 118. For example, given the relationships of cross-sectional area discussed above, the velocity of the fluid flow through the distal section 302 will be between one percent (1%) and thirty percent (30%) faster than the velocity through the proximal section 304, and in some cases at least twenty percent (20%) faster. Moreover, for the same constant fluid flow rate, the velocity within the aperture 206 through the active electrode 202 will be faster than through the distal section 302 of the aperture 208, but again as the aperture 206 etches and thus becomes larger, the velocity through the aperture 208 approaches that of the distal section 302. Initially, however, the velocity of the fluid through the aperture 206 may be at least ten percent (10%) faster than the velocity through the distal section 302.

The various embodiments regarding the wand 102 to this point have assumed that the cross-sectional shape of the aperture 206 matches or approximates the cross-sectional shape of the distal section 302 of the aperture 208, and likewise the cross-sectional shape of the distal section 302 of the aperture 208 matches the cross-sectional shape of the proximal section 304 of the aperture 208. However, in other embodiments the cross-sectional shapes need not match as between the various apertures. For example, the aperture 206 may be circular in cross-section, but the sections 302 and 304 of the aperture 208 may each define a quadrilateral (e.g., square, rectangle). By way of further example, the aperture 206 may be star shaped in cross-section, but the sections 302 and 304 of the aperture 208 may each define a circular cross-section. Moreover, the sections 302 and 304 of the aperture 208 likewise need not define the same cross-sectional shape. Thus, in some cases the differences in size of the apertures may be expressed in terms of a largest dimension measured along a straight line. For example, in some cases the largest dimension of the aperture 206 through the conductive electrode 202 is between one percent (1%) and twenty percent (20%) smaller than the largest dimension of the distal section 302 of the aperture 208, and in a particular case at least fifteen percent smaller (15%).

FIG. 3a also shows an illustrative electrical coupling regarding the active electrode 202. In particular, the active electrode 202 defines an inner surface 310 that abuts the distal end of the spacer 200. The illustrative active electrode 202 also defines legs that extend into counter bores of the spacer. For example, the active electrode defines leg 312 that extends into counter bore 314 of the spacer. In some cases, the leg 312 is a press fit within counter bore 312, but in other cases an adhesive 316 may be used. As there is no electrical connection associated with leg 312, the connection of leg 312 to the spacer 200 may provide only mechanical support for the active electrode 202, such as to hold the active electrode in the abutting relationship with the spacer 200. FIG. 3a also shows leg 318 extending into bore 320. As before, an adhesive 322 may also be present to secure the leg 318 in the bore. Unlike leg 312, however, leg 318 also electrically couples to an insulated conductor 324 that extends through the bore 320. Thus, energy provided to the active electrode 202 may be transmitted through the insulated conductor 324. Thus, with respect to leg 318 the adhesive 322 may not only provide mechanical support, but also seal the bore 320.

Figure 3B:
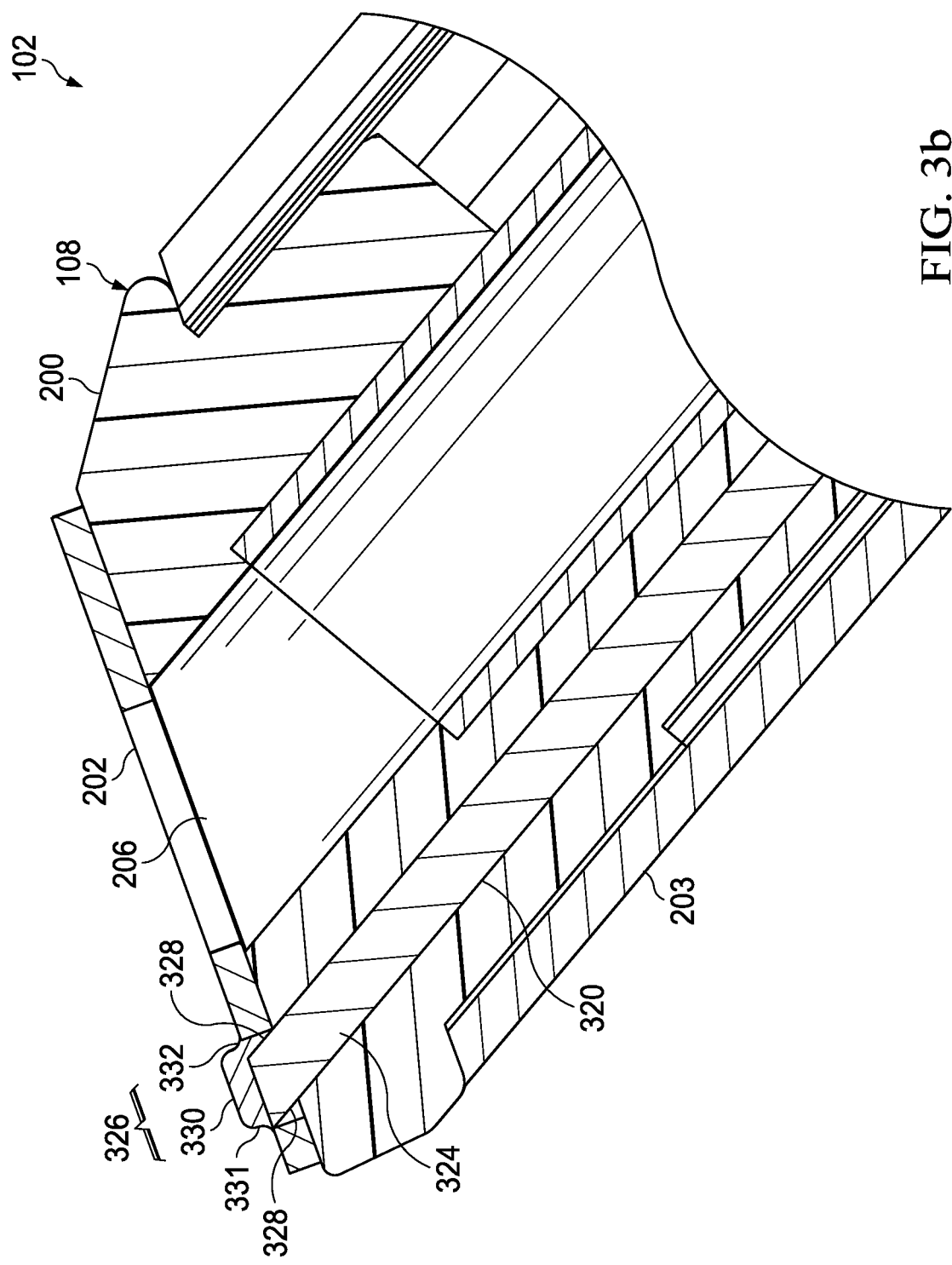

FIG. 3b shows an alternative electrical coupling regarding the active electrode 202. Electrical conductor 324 extends through shaft 106 and bore 320 in spacer 200 to active electrode 202 to electrically couple active electrode 202. Active electrode 202 is mounted to spacer 200 so that a portion 326 of conductor 324 extends through holes in active electrode 202 and bore 320. Portion 326 may extend above the surface of active electrode 202 approximately between 0.006 inches and 0.015 inches or less. Portion 326 of conductor 324 is then laser welded to form weld 330 at the surface of active electrode 202 (see also FIG. 2b). Weld 330 is formed with smooth transition portions 331 and 332 between weld 330 and active electrode 202 in order to make weld 330 less likely to promote plasma formation at the transition portions 331 and 332. Transition portion 331 and 332 are such that they are free of rough surfaces, edges, or other asperities, so as to avoid plasma formation thereon. Weld 330 functions to electrically couple and mechanically secure active electrode 202 onto spacer 200. Additionally, certain amounts 328 of portion 326 of conductor 324 may flow into the holes in active electrode 202 during the laser welding process, such that mechanical and electrical connection between the active electrode 202 and conductor 324 also occurs inside the holes of active electrode 202. In certain embodiments, a length of conductor 324 may be used to form only a mechanical connection to secure active electrode 202 to spacer 200. In these configurations, conductor 324 is formed in a U-shaped configuration such that each free end of conductor 324 is extended through active electrode 202 at a respective location and then laser welded to active electrode 202. The inventors of the present specification have found that it is beneficial to construct active electrode 202 of tungsten and conductor 324 of titanium or platinum in order to enhance the joining properties of weld 330 in this configuration. Additionally, the inventors of the present specification have found that it is beneficial to position the several welds 330 used to secure and connect active electrode 202 at locations spaced away from the edges of active electrode 202 and aperture 206 in order to enhance the wear and life of welds 330.

Figure 4A:
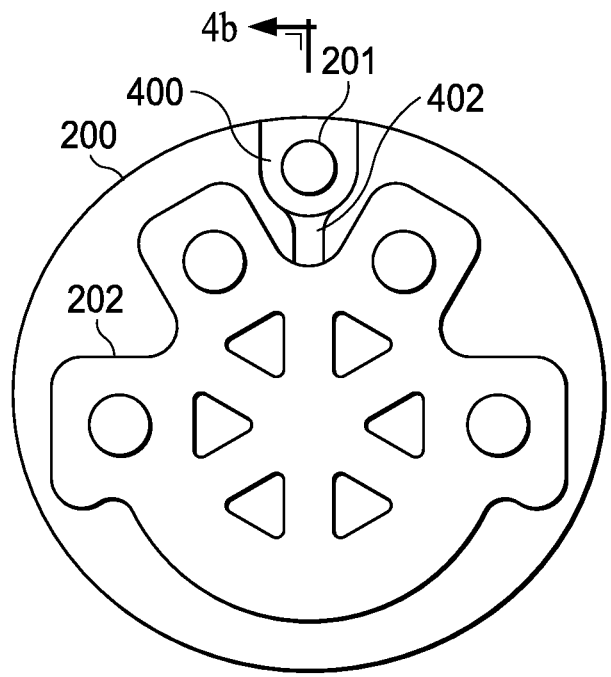
FIGS. 4a and 4b shows a perspective view of the distal end of a wand in accordance with at least some embodiments.
Figure 4B:
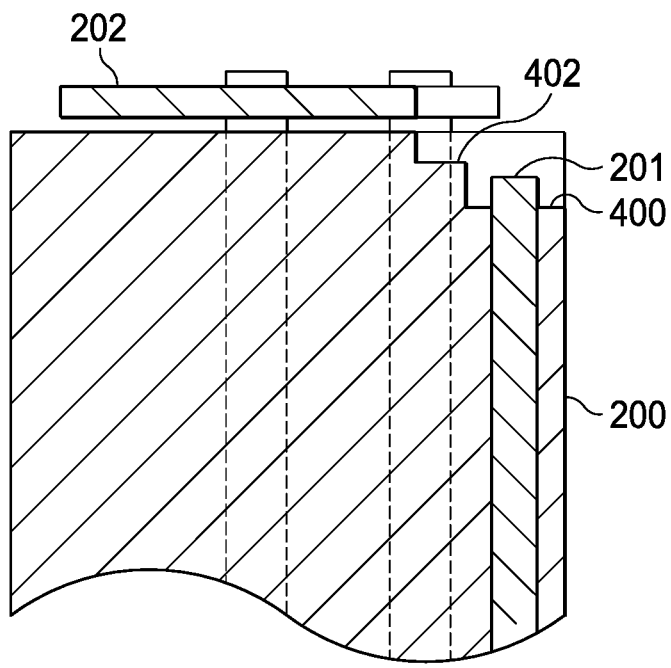

FIGS. 4a and 4b shows a perspective view of a distal end 108 of a wand 102 in accordance with yet still further example systems. In particular, FIG. 4a shows active electrode 202 disposed on the spacer 200. Moreover, FIG. 4a shows pilot electrode 201 located within recess 400 of spacer 200 and disposed adjacent to active electrode 202 with channel 402 in communication with recess 400. Pilot electrode 201 is defined by a single, wire shaped conductor, while active electrode 202 is defined by a flat, screen shaped conductor. The inventors of the present specification have found that a configuration having two or more electrode of various sizes that are activated asynchronously may be beneficial to operation of the electrosurgical effect. This arranged is in contrast to current systems that use only a single active electrode, or several active electrodes that are activated synchronously, where the only manner to reduce the amount of power dissipation is to reduced the size of the electrode and/or to reduce the amount of fluid flow over the electrode(s).

The principle of this arrangement between two active electrodes with varying sizes as described in the present embodiment is to control the electrode surface area of the one active electrode in contact with low impedance conductive fluid. This is achieved by activating separately through independent output channels two or more active electrodes in a consecutive, but non-synchronous fashion such that sufficient vapor coverage is obtained on the initially activated electrode before the next active electrode is energized, therefore preventing having a large surface area exposed to the conductive fluid and therefore limiting the overall current dissipation. Accordingly, in the present embodiment pilot electrode 201 is generally smaller in size as compared to active electrode 202, but other comparative sizes are contemplated and may be used equivalently. Pilot electrode 201 is first activated, generating some vapor layer according to the electrosurgical principles described herein, such that the vapor layer that will progressively cover the active electrode(s) 202 via migration through channel 402. Active electrode 202 can then be subsequently activated with a small time delay, where the delay can be automatically controlled by measuring the impedance of the circuit of the active electrode 202 with the return electrode 203, and trigger the activation of active electrode 202 when the measured electrode circuit impedance reaches a certain threshold. As described above, smaller pilot electrode 201 is positioned within recess 400 in order to prevent the bubble of vapor layer (i.e., the plasma) from being extinguished due to fluid flow over the tip of the device. Thereby, stable activation of the pilot electrode 201 is maintained independently of whether active electrode 202 is energized. In instances where the vapor layer formed on active electrode 202 is extinguished, thereby resulting in the active electrode 202 being fully exposed to the field of circulating conductive fluid and the current reaching a level that forces the RF output to be turned off, the pilot electrode 201 remains energized and sustaining a vapor layer. Active electrode 202 may then be activated when it is sufficiently covered with gas or vapor to prevent undesired current dissipation that occurs with a state of extinguishing plasma.

In another related embodiment, the flow of fluid across or over the active electrode 202 is controlled by a peristaltic pump 118 (see FIG. 1), the flow over the active electrode 202 will be stopped or reduced until it is sufficiently covered by a layer of gas or vapor. Reestablishing the layer of gas or vapor is assisted by the cessation of fluid flow over the active electrode 202 and/or by the presence of the continual vapor layer formed on adjacent pilot electrode 201. In order to maximize the performance of the system according to these embodiments, each of the pilot electrode 201 and active electrode 202 needs to be powered by an independent power supply or output stage that also monitors the impedance of the electrode circuit. In some cases, it may be helpful to activate various active electrodes 202 at different amplitudes of pulse width such that a layer of vapor is created, but while limiting the total amount of power or current dissipated, such that only the active electrode(s) 202 with a suitably high electrode circuit impedance (i.e., indicative of a stable vapor layer on the surface of that electrode) would be activated with full amplitude and/or pulse width.

During arthroscopic surgical procedures the visual field near the surgical site (i.e., near the active electrode) may have a tendency to be obscured by gas bubbles. That is, the process of ablation creates gas bubbles, and in many situations the gas bubbles are quickly aspirated away so as not adversely affect the visual field. However, in other situations (e.g., when the primary aperture is momentarily occluded by tissue), gas bubbles may accumulate in the vicinity of the surgical site thus blocking the visual field. The example wand 102 discussed with respect to FIG. 5 below has additional features which reduces accumulation of gas bubbles in the vicinity of the surgical site. In particular, the example features include slots in the active electrode, and in some cases flow channels defined in the spacer where the flow channels form apertures near the outer perimeter of the active electrode. The slots are designed and constructed such that substantially only gasses pass through the slots. That is, the size of the slots is selected such that the size of tissue in the surgical field (even disassociated tissue created during an ablation) is too large for the tissue to pass through the slots. Likewise, surface tension of liquid (e.g., saline, blood, cellular fluids) is too great for the liquids to pass through the slots. Thus, the slots enable aspiration only of gasses. In this way, the slots do not adversely affect the ablation characteristics of an active electrode, but nevertheless may help aspirate the bubbles away from the surgical field in some situations, particularly when the primary aperture is fully or partially blocked.

Figure 5:
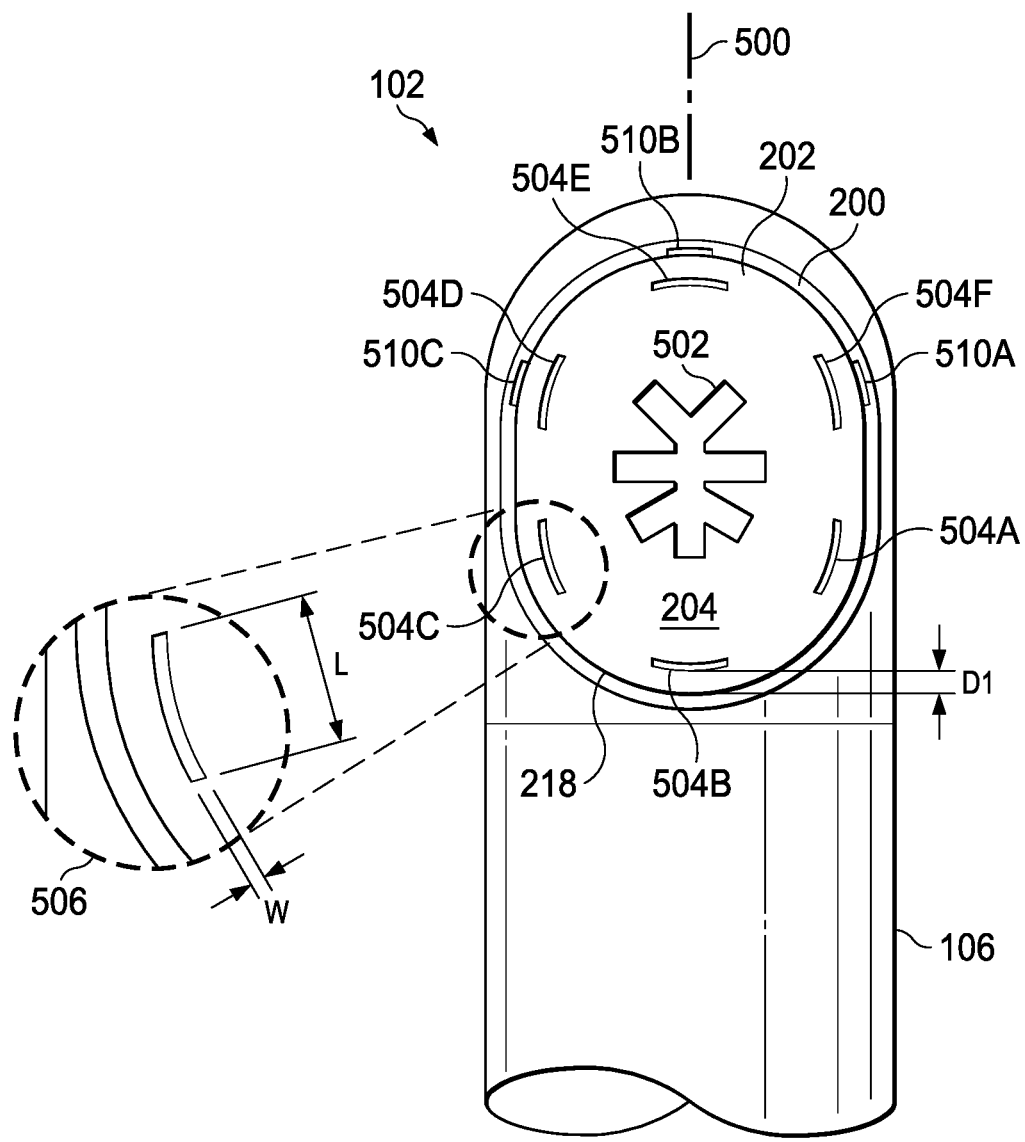
FIG. 5 shows an elevation view of the distal end of a wand in accordance with at least some embodiments.

FIG. 5 shows an elevation view of a distal end of wand 102 in accordance with the further example systems. In particular, FIG. 5 shows elongate shaft 106 and active electrode 202 abutting a spacer 200 of non-conductive material. The outer surface 204 of the active electrode 202 in FIG. 5 defines a plane that is parallel to the plane of page. For the example of FIG. 5, the elongate shaft 106 defines a central axis 500, and the plane defined by the outer surface 204 of the active electrode is parallel to the central axis 500. However, the various features of the wand 102 of FIG. 5 discussed more below are not limited to wands where the outer surface 204 is parallel to the central axis 500, and thus may be used, for example, with the wands shown in FIGS. 2a and 2b.

Visible in FIG. 5 is primary aperture 502 through the active electrode 202, which aperture 502 is at least partially aligned with an aperture through the spacer 200 (the aperture through the spacer not visible in FIG. 5), and both the aperture 502 and aperture through the spacer 200 are fluidly coupled to the flexible tubular member 116 (also not visible in FIG. 5). The example primary aperture 502 of FIG. 5 has plurality of asperities, which asperities may help in the initial formation of plasma. The aperture 502 is merely illustrative, and circular, star-shaped, and/or oval apertures previously discussed may be equivalently used with the example wand of FIG. 5.

Active electrode 202 of FIG. 5 further comprises a plurality of slots 504. Six such slots are shown, but one or more slots are contemplated. Each slot 504 is an aperture that extends through the active electrode 202, but the slots 504 serve a specific purpose of aspirating bubbles near the active electrode, and will be referred to as slots in this specification rather than apertures to logically distinguish from the other apertures (such as primary aperture 502 in FIG. 5, or primary aperture 206 of the previous example wands). Each of the slots 504 is positioned parallel to the outer perimeter 218 of the active electrode, but other arrangements of the slots are contemplated. In some cases, the distance D1 between each slot and the outer perimeter 218 of the may be between and including 0.008 and 0.010 inch (0.2032 and 0.254 mm). Thus, the slots 504 are disposed closer to the outer perimeter 218 than the aperture 502 is to the outer perimeter 218. The example slots 504 are disposed about the primary aperture 502. For example, slot 504A is disposed on one side of the aperture 502, while slots 504C and 504D are disposed on an opposite side of the primary aperture. Likewise, slot 504B is disposed on an opposite side of the aperture 502 from the slot 504E. In one example system (not specifically shown), a single slot 504 is present, where the single slot fully encompasses the aperture 502.

Still referring to FIG. 5, and in particular the magnified section 506 showing slot 504C in greater detail. Each slot defines a length L and width W, and for each slot the length L is at least twice as long as the width W. The length L range of a slot may span from as small as 0.002 inches (0.0508 mm) to a length long enough to fully encircle the aperture 502. It is noted that in the case where a single slot fully encircles the aperture 502, the outer surface 204 of the active electrode 202 may be non-contiguous and thus the active electrode 202 may comprise two components (a portion outside the slot and a portion inside the slot). The width W of a slot is selected such that substantially only gasses may pass through the slots, and with tissue and liquids being too large to pass through slots. In example systems, the width W of the slots and may be between and including 0.001 to 0.003 inch (0.0254 to 0.0762 mm), and in a particular case between 0.001 and 0.002 inch (0.0254 to 0.0508 mm). While in some cases the width W of each slot is the same, in other cases different slots may have different widths on the same active electrode. Each slot is fluidly coupled to the flexible tubular member 116, and various example systems of the fluid connections are discussed more below.

In operation, during periods of time when the primary aperture 502 is not blocked, it is likely that few, if any, gas bubbles will be drawn into slots. That is, the path of least resistance for the movement of bubbles and liquids will be into the primary aperture 502, and then into corresponding aperture in the spacer 200. However, during periods of time when the primary aperture 502 is fully or partially blocked, a volume controlled aspiration results in an increased vacuum applied by the peristaltic pump 118. Periods of increased vacuum (with the primary aperture fully or partially blocked) may result in sufficient differential pressure across the slots to draw gas bubbles through the slots. Thus, during periods of time when bubbles tend to accumulate and obscure the visual field (i.e., during full or partial blockage of the primary aperture), the slots tend to reduce the visual affect by removing gas bubbles from the visual field.

Still referring to FIG. 5, in some example systems, the spacer defines flow channels beneath and substantially parallel to the active electrode 202. The flow channels are fluidly coupled to the flexible tubular member 116, in some cases by way of the main aperture through the spacer 200. The flow channels are shown, and discussed further, with respect to FIG. 6 below. In some cases, however, the flow channels define apertures that abut the outer perimeter 218 of the active electrode. For example, FIG. 5 shows three such apertures 510A, 510B, and 510C, but one or more such apertures 510 may be used. The apertures 510 may be used to aspirate both gasses and liquids proximate to the outer perimeters 218 of the active electrode, and thus may also reduce the obscuration of the visual field.

Figure 6:
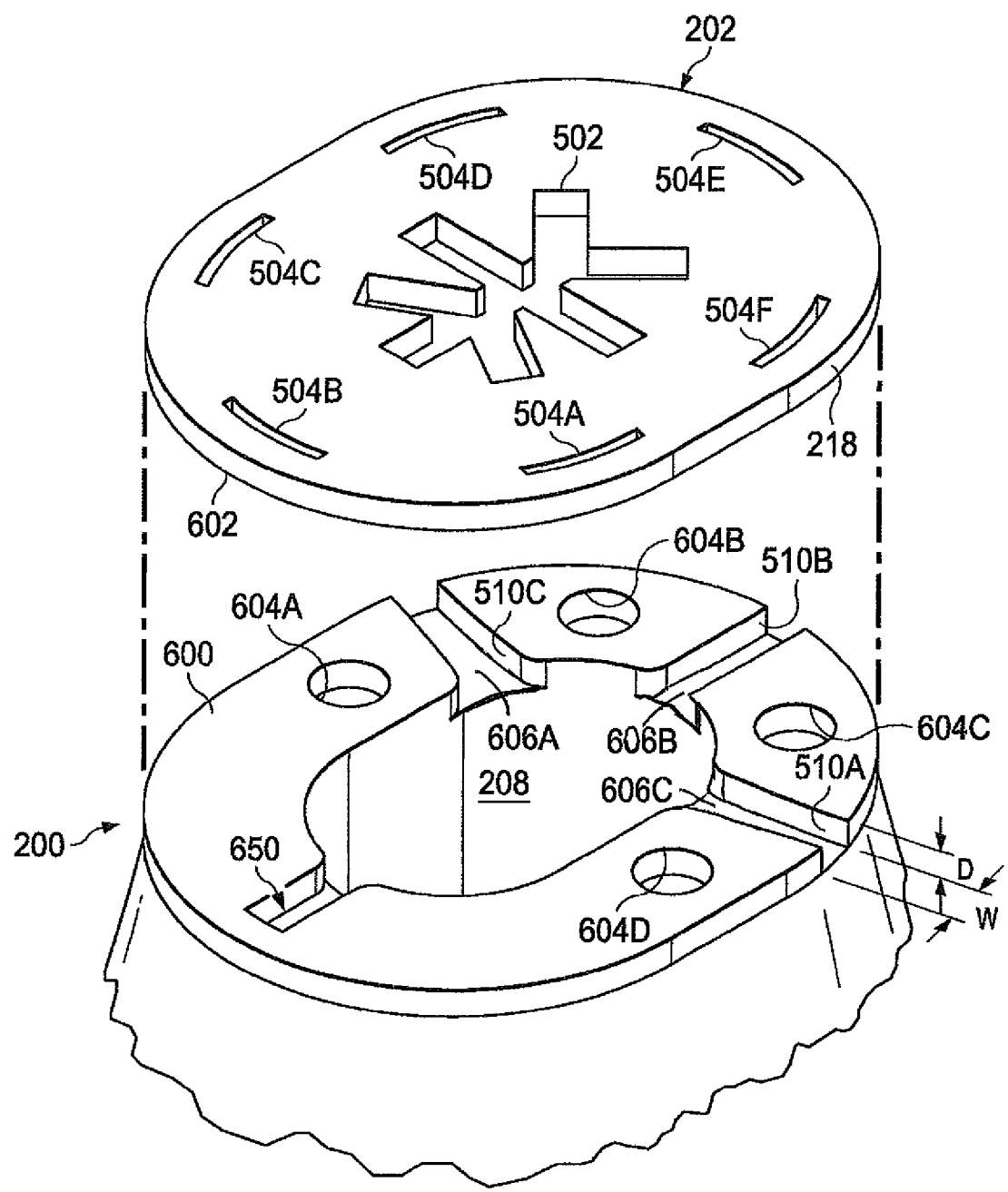
FIG. 6 shows an exploded perspective view of a the distal end of a wand in accordance with at least some embodiments.

FIG. 6 shows an exploded perspective view of the active electrode 202 and spacer in these example embodiments. In particular, FIG. 6 shows spacer 200 below active electrode 202, however when assembled the active electrode 202 abuts the spacer 200. That is, the spacer 200 in these cases defines a planar face 600. An inner surface 602 of the active electrode (as opposed to the outer surface 204) likewise defines a plane, and when assembled the inner surface 602 of the active electrode 202 abuts the planar face 600. The active electrode 202 may mechanically couple to the spacer 200 by any suitable mechanism. In one case, the active electrode 202 may both mechanically and electrically couple by way of apertures 604A-D. That is, at least one of the apertures 604 may comprise an electrical conductor that electrically couples to the active electrode 202 through the aperture, and the electrical conductor may at least partially mechanically hold the active electrode 202 against the spacer 200. Additional mechanical elements may likewise extend from the active electrode 202 into the apertures 604 of the spacer 200 and be held in place, such as by epoxy. Additional apertures and features may be present on the active electrode associated with the electrical and mechanical coupling to the spacer 200, but these additional apertures and features are not shown so as not to unduly complicate the figure.

The spacer 200 further defines a primary aperture 208 in operational relationship to the primary aperture 502 of the active electrode 202. Though not visible in FIG. 6, in some example systems the aperture 208 in the spacer 200 defines an increasing cross-sectional area with distance along aspiration path toward the proximal end 110 of the wand. The example spacer 200 further comprises a plurality of flow channels 606A-C. When the active electrode 202 abuts the spacer 200, each flow channels 606A, 606B, and 606C may reside at least partially beneath the slots 504D, 504E, and 504F, respectively. While three slots are shown to be associated with flow channels, any number of slots may be associated with flow channels, including all the slots, and thus greater or fewer flow channels may be defined in the spacer 200. During periods of time when gas bubbles are being drawn through slots 504D-F associated with flow channels, the flow path for the gas bubbles includes the respective flow channels 606A-C, and then the primary aperture 208 in the spacer 200. For slots that are not associated with flow channels (e.g., 504B and 504C), during periods of time when gas bubbles are being drawn through slots 504A-C the flow path for the gas bubbles includes the space defined between the active electrode 202 and the spacer 200, and then the primary aperture 208 in the spacer 200.

In some cases, each flow channel defines a depth D (as measured from the planar surface 600 to the bottom of the channel at the distal end of the channel) of between and including 0.007 and 0.008 inch (0.1778 to 0.2032 mm), and a width W (again as measured at the distal end of the channel) of 0.007 and 0.008 inch (0.1778 to 0.2032 mm), but other sizes may be used. Consistent with the philosophy regarding increasing cross-sectional area, the flow channels may define a distal cross-sectional area (e.g., under the respective slot), and likewise define a proximal cross-sectional area (e.g., closer to the primary aperture 208), and the distal cross-sectional area is smaller than the proximal cross-sectional area.

As illustrated in FIG. 6, in some cases the flow channels 606 extend to the outer perimeter 218 of the active electrode 200, and thus the distal ends of the flow channels define the apertures 510. In other cases, however, the flow channels may extend only as far as needed toward the outer perimeter 218 to reside under respective slots 504, and thus the presence of a flow channel 606 in spacer 200 does not necessitate the presence of apertures 510. In the example of FIG. 5, flow channel 650 extends outward to reside under slot 504B, but does not extend to the outer perimeter 218 of the active electrode 202. Flow channel 650 defines a constant cross-sectional area along the flow channel until the primary aperture is reached, as the likelihood of tissue entering the flow channels through the respective slots 504 alone is relatively small, and thus clogging is not as big a concern.

While the example flow channels 606 and 650 are fluidly coupled directly to the primary aperture 208, the flow channels need not be so constructed. For example, the spacer may define apertures associated with some or all the slots 504, where the apertures run substantially parallel to the primary aperture 208, and eventually fluidly couple to the aspiration path within the elongate shaft 106. Moreover, FIG. 6 shows examples of slots 504 with corresponding flow channels 606 (i.e., slots 504B and 504D-F), and slots 504 that do not have flow channels (i.e., slots 504A and 504C), so as to describe example situations; however, wands with slots and no flow channels are contemplated, as are wands where every slot is associated with a flow channel. Where flow channels are used, any combination of the number of flow channels that extend to the outer perimeter 218 of the active electrode 202, from none of the flow channels to all the flow channels, may also be used. Finally, while active electrodes with slots may find more functionality in cases where no standoffs are used, the slots and standoffs are not mutually exclusive—any combination of slots and standoffs that provides an operational advantage may be used.

Figure 7:
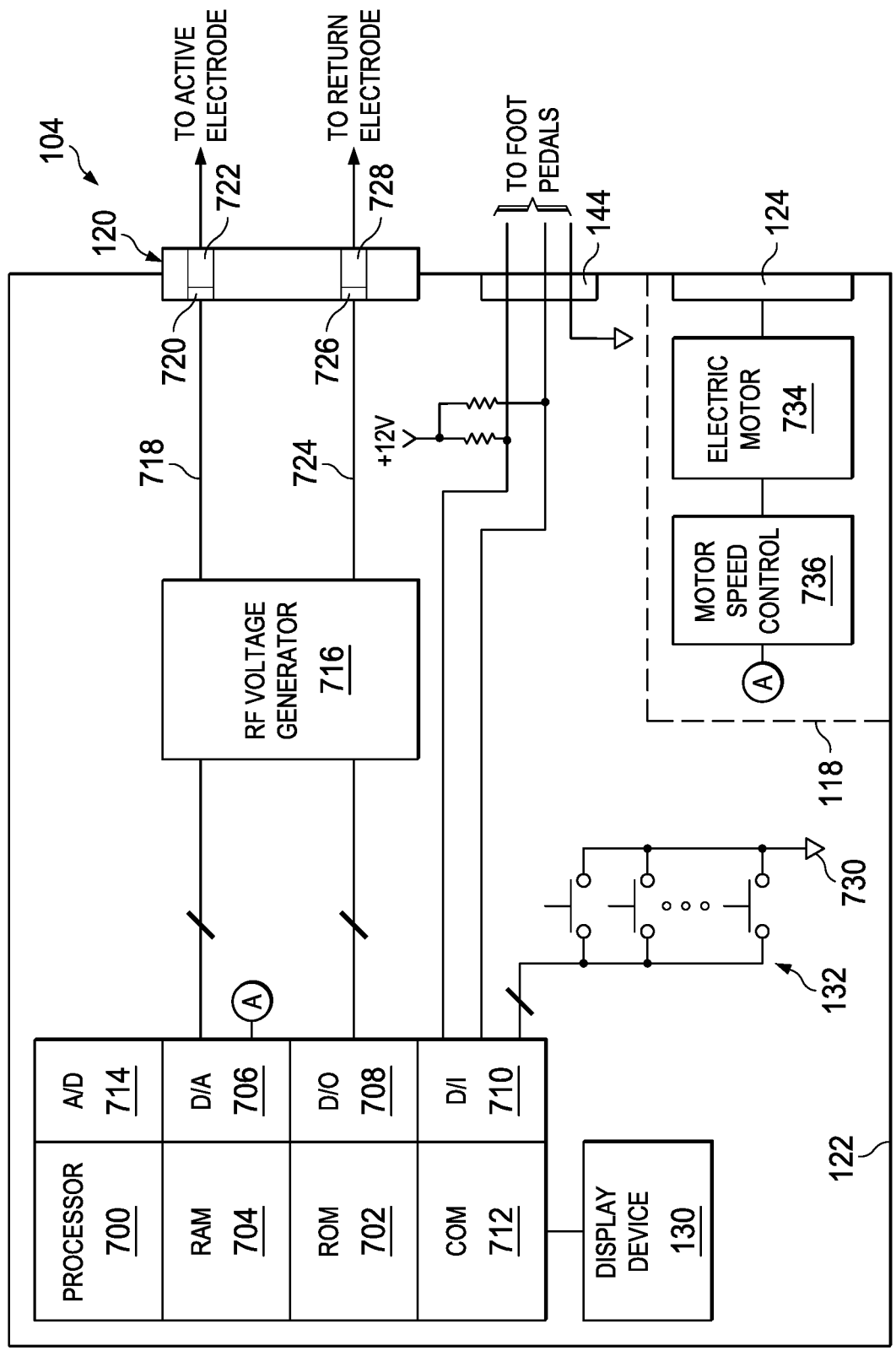
FIG. 7 shows an electrical block diagram of an electrosurgical controller in accordance with at least some embodiments.

FIG. 7 shows an electrical block diagram of controller 104 in accordance with at least some embodiments. In particular, the controller 104 comprises a processor 700. The processor 700 may be a microcontroller, and therefore the microcontroller may be integral with read-only memory (ROM) 702, random access memory (RAM) 704, digital-to-analog converter (D/A) 706, analog-to-digital converter (A/D) 714, digital outputs (D/O) 708, and digital inputs (D/I) 710. The processor 700 may further be integral with communication logic 712 to enable the processor 700 to communicate with external devices, as well as internal devices, such as display device 130. Although in some embodiments the processor 700 may be implemented in the form of a microcontroller, in other embodiments the processor 700 may be implemented as a standalone central processing unit in combination with individual RAM, ROM, communication, A/D, D/A, D/O, and D/I devices, as well as communication hardware for communication to peripheral components.

ROM 702 stores instructions executable by the processor 700. In particular, the ROM 702 may comprise a software program that, when executed, causes the controller to deliver RF energy to the active electrode and control speed of the peristaltic pump. The RAM 704 may be the working memory for the processor 700, where data may be temporarily stored and from which instructions may be executed. Processor 700 couples to other devices within the controller 104 by way of the digital-to-analog converter 706 (e.g., in some embodiment the RF voltage generator 716), digital outputs 708 (e.g., in some embodiment the RF voltage generator 716), digital inputs 710 (e.g., interface devices such as push button switches 132 or foot pedal assembly 134 (FIG. 1)), and communication device 712 (e.g., display device 130).

Voltage generator 716 generates an alternating current (AC) voltage signal that is coupled to active electrode 202 of the wand 102. In some embodiments, the voltage generator defines an active terminal 718 which couples to electrical pin 720 in the controller connector 120, electrical pin 722 in the wand connector 114, and ultimately to the active electrode 202. Likewise, the voltage generator defines a return terminal 724 which couples to electrical pin 726 in the controller connector 120, electrical pin 728 in the wand connector 114, and ultimately to the return electrode (in some cases, a metallic elongate shaft 106). Additional active terminals and/or return terminals may be used. The active terminal 718 is the terminal upon which the voltages and electrical currents are induced by the voltage generator 716, and the return terminal 724 provides a return path for electrical currents. It would be possible for the return terminal 724 to provide a common or ground being the same as the common or ground within the balance of the controller 104 (e.g., the common 730 used on push-buttons 132), but in other embodiments the voltage generator 716 may be electrically "floated" from the balance of the controller 104, and thus the return terminal 724, when measured with respect to the common or earth ground (e.g., common 730) may show a voltage; however, an electrically floated voltage generator 716 and thus the potential for voltage readings on the return terminals 724 relative to earth ground does not negate the return terminal status of the terminal 724 relative to the active terminal 718.

The AC voltage signal generated and applied between the active terminal 718 and return terminal 724 by the voltage generator 716 is RF energy that, in some embodiments, has a frequency of between about 5 kilo-Hertz (kHz) and 20 Mega-Hertz (MHz), in some cases being between about 30 kHz and 2.5 MHz, in other cases being between about 50 kHz and 500 kHz, often less than 350 kHz, and often between about 100 kHz and 200 kHz. In some applications, a frequency of about 100 kHz is useful because target tissue impedance is much greater at 100 kHz.

The RMS (root mean square) voltage generated by the voltage generator 716 may be in the range from about 5 Volts (V) to 1800 V, in some cases in the range from about 10 V to 500 V, often between about 10 V to 400 V depending on the mode of ablation and active electrode size. The peak-to-peak voltage generated by the voltage generator 716 for ablation in some embodiments is a square waveform with a peak-to-peak voltage in the range of 10 V to 2000 V, in some cases in the range of 100 V to 1800 V, in other cases in the range of about 28 V to 1200 V, and often in the range of about 100 V to 320V peak-to-peak.

The voltage and current generated by the voltage generator 716 may be delivered in a series of voltage pulses or AC voltage with a sufficiently high frequency (e.g., on the order of 5 kHz to 20 MHz) such that the voltage is effectively applied continuously (as compared with, e.g., lasers claiming small depths of necrosis, which are pulsed about 10 Hz to 20 Hz). In addition, the duty cycle (i.e., cumulative time in any one-second interval that energy is applied) of a square wave voltage produced by the voltage generator 716 is on the order of about 50% for some embodiments as compared with pulsed lasers which may have a duty cycle of about 0.0001%. Although square waves are generated and provided in some embodiments, the AC voltage signal is modifiable to include such features as voltage spikes in the leading or trailing edges of each half-cycle, or the AC voltage signal is modifiable to take particular shapes (e.g., sinusoidal, triangular).

Still referring to FIG. 7, controller 104 in accordance with various embodiments further comprises the peristaltic pump 118. The peristaltic pump 118 may reside at least partially within the enclosure 122. The peristaltic pump comprises the rotor 124 mechanically coupled to a shaft of the motor 734. In some cases, and as illustrated, the rotor of the motor may couple directly to the rotor 124, but in other cases various gears, pulleys, and/or belts may reside between the motor 734 and the rotor 124. The motor 734 may take any suitable form, such as an AC motor, a DC motor, and/or a stepper-motor. To control speed of the shaft of the motor 734, and thus to control speed of the rotor 124 (and the volume flow rate at the wand), the motor 734 may be coupled to a motor speed control circuit 736. In the illustrative case of an AC motor, the motor speed control circuit 736 may control the voltage and frequency applied to the electric motor 734. In the case of a DC motor, the motor speed control circuit 736 may control the DC voltage applied to the motor 734. In the case of a stepper-motor, the motor speed control circuit 736 may control the current flowing to the poles of the motor, but the stepper-motor may have a sufficient number of poles, or is controlled in such a way, that the rotor 124 moves smoothly.

The processor 700 couples to the motor speed control circuit 736, such as by way of the digital-to-analog converter 706 (as shown by bubble A). The processor 700 may be coupled in other ways as well, such as packet-based communication over the communication port 712. Thus, the processor 700, running a program, may determine RF energy supplied on the active terminal 718, and responsive thereto may make speed control changes (and thus volume flow rate changes) by sending speed commands to the motor speed control circuit 736. The motor speed control circuit 736, in turn, implements the speed control changes. Speed control changes may comprise changes in speed of the rotor 124 when desired, stopping the rotor 124 when desired, and in some modes of ablation temporarily reversing the rotor 124.

Figure 8:
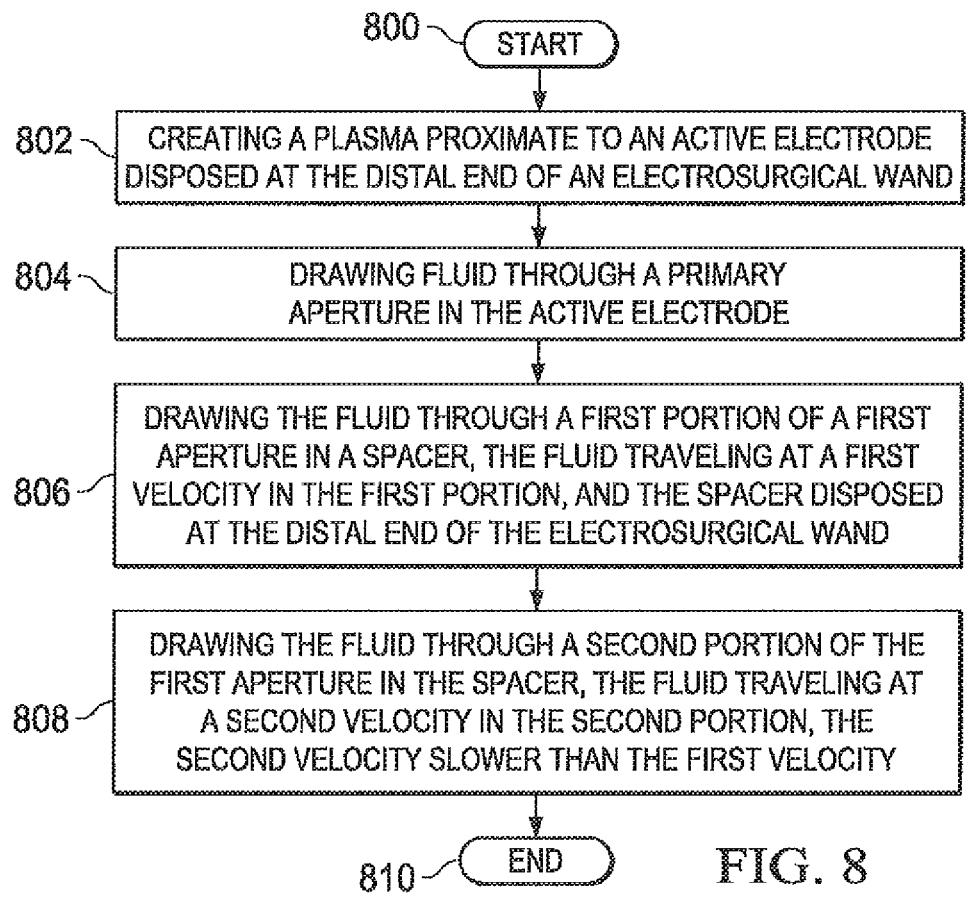
FIG. 8 shows a method in accordance with at least some embodiments.

FIG. 8 shows a method in accordance with at least some embodiments. In particular, the method starts (block 800) and proceeds to: creating a plasma proximate to an active electrode disposed at the distal end of an electrosurgical wand (block 802); drawing fluid through a primary aperture in the active electrode (block 804); and drawing the fluid through a first portion of a first aperture in a spacer (block 806), the fluid traveling at a first velocity in the first portion, and the spacer disposed at a distal end of the electrosurgical wand; and drawing the fluid through a second portion of the first aperture in the spacer (block 808), the fluid traveling at a second velocity in the second portion, the second velocity slower than the first velocity. Thereafter, the method ends (block 810).

Figure 9:
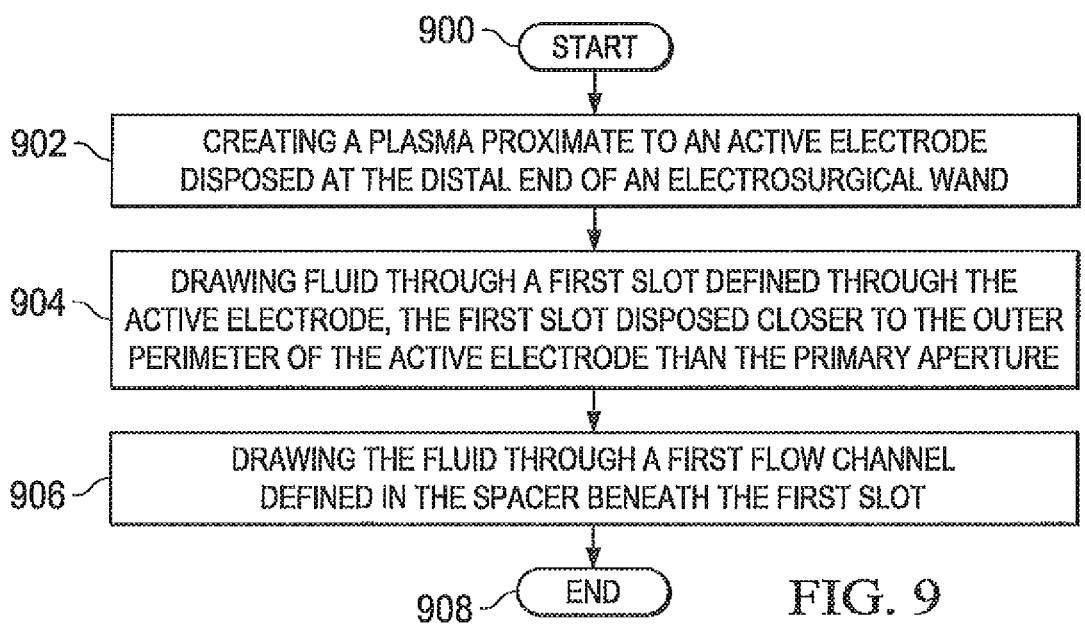
FIG. 9 shows a method in accordance with at least some embodiments.

FIG. 9 shows a method in accordance with at least some embodiments. In particular, the method starts (block 900) and proceeds to: creating a plasma proximate to an active electrode disposed at the distal end of an electrosurgical wand (block 902); drawing fluid through a first slot defined through the active electrode (block 904), the first slot disposed closer to the outer perimeter of the of the active electrode than the primary aperture; drawing the fluid through a first flow channel defined in the spacer beneath the first slot (block 906). Thereafter, the method ends (block 908).

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. A method comprising:
   creating a plasma proximate to an active electrode disposed at a distal end of an electrosurgical wand, the active electrode having a planar tissue treatment surface;
   drawing fluid through a primary aperture through the planar tissue treatment surface of the active electrode; and then
   drawing the fluid through a primary lumen in a spacer, the spacer disposed at a distal end of the electrosurgical wand; and
   drawing the fluid along a fluid flow path and then through the primary lumen, the fluid flow path beginning at a fluid inlet perpendicularly orientated relative to the planar tissue treatment surface, the fluid flow path defined by opposing mating surfaces including an inner surface of the active electrode and spacer distal surface such that the fluid flow path is limited to flow parallel to the active electrode inner surface by a planar face of the spacer until the fluid flow path reaches the primary lumen.

2. The method of claim 1 further comprising:
   drawing fluid through a first slot defined through the active electrode, the first slot disposed closer to an outer perimeter of the active electrode than the primary aperture and spaced away from the active electrode outer perimeter.

3. The method of claim 2 further comprising:
   drawing the fluid through a second slot defined through the active electrode, the second slot disposed closer to and not coincident with the outer perimeter than the primary aperture, the second slot disposed on an opposite side of the primary aperture from the first slot.

4. The method of claim 2 wherein drawing fluid through the first slot further comprises:
   drawing the fluid through a portion of the fluid flow path disposed beneath the first slot.

5. The method of claim 4 wherein the fluid inlet defines an outer aperture that abuts the outer perimeter of the active electrode.

6. The method of claim 1 wherein the fluid inlet includes an outer perimeter of the active electrode.

7. The method of claim 6 wherein the fluid flow path extends from the active electrode outer perimeter in a radial direction.

8. A method comprising:
   creating a vapor layer proximate to an active electrode disposed at a distal end of an electrosurgical wand;
   drawing fluid through a primary aperture in the active electrode; and then through a primary lumen in a spacer; and
   drawing the fluid along a gap defined by abutting surfaces of an inner surface of the active electrode and a spacer planar surface, the gap extending substantially parallel to a tissue treatment surface of the active electrode and fluidly coupled to the primary lumen in the spacer.

9. The method of claim 8 wherein the gap defines an opening at a peripheral edge surface of the active electrode.

10. The method of claim 8 wherein the gap defines an opening defined by a peripheral edge surface of the active electrode and a peripheral edge surface of the spacer.

11. The method of claim 8 wherein the gap extends to the primary lumen in the spacer.

12. A method comprising:
    supplying energy to an active electrode disposed at a distal end of an electrosurgical wand in the presence of an electrically conductive fluid;
    drawing a portion of the electrically conductive fluid through a first fluid path defined by a primary aperture in the active electrode and a lumen disposed through a spacer; and
    drawing a second portion of the electrically conductive fluid along a second fluid path that includes an outer periphery of the active electrode, the second fluid path also extending beneath the active electrode through a flow channel within the spacer that is substantially parallel to a planar tissue treatment surface of the active electrode, followed by extending into an aperture of the lumen disposed through the spacer, the aperture coincident with an active electrode inner surface.

13. The method of claim 12 wherein the second fluid path includes an outer aperture defined by an outer-most surface of the spacer, the outer aperture on a plane substantially perpendicular to the planar tissue treatment surface.

14. The method of claim 12 wherein the second fluid path defines a cross-section that is non-uniform as it extends beneath the active electrode.

15. The method of claim 12 wherein the second fluid path is defined by a spacer distal end surface and the inner surface of the active electrode.

* * * * *